(12) United States Patent
Thomas

(10) Patent No.: US 11,351,110 B2
(45) Date of Patent: Jun. 7, 2022

(54) SILICONE-FREE COSMETIC COMPOSITIONS

(71) Applicant: Kirsten Elizabeth Thomas, San Juan Capistrano, CA (US)

(72) Inventor: Kirsten Elizabeth Thomas, San Juan Capistrano, CA (US)

(73) Assignee: Kirsten Elizabeth Thomas, San Juan Capistrano, CA (US)

( * ) Notice: Subject to any disclaimer, the term of this patent is extended or adjusted under 35 U.S.C. 154(b) by 8 days.

(21) Appl. No.: 16/904,355

(22) Filed: Jun. 17, 2020

(65) Prior Publication Data

US 2020/0397688 A1 Dec. 24, 2020

Related U.S. Application Data

(60) Provisional application No. 62/865,011, filed on Jun. 21, 2019.

(51) Int. Cl.
*A61K 36/00* (2006.01)
*A61K 8/9789* (2017.01)
*A61K 8/9794* (2017.01)
*A61K 8/92* (2006.01)
*A61K 8/37* (2006.01)
*A61Q 19/00* (2006.01)
*A61Q 5/12* (2006.01)

(52) U.S. Cl.
CPC .............. *A61K 8/9789* (2017.08); *A61K 8/37* (2013.01); *A61K 8/922* (2013.01); *A61K 8/9794* (2017.08); *A61Q 5/12* (2013.01); *A61Q 19/007* (2013.01); *A61K 2800/10* (2013.01); *A61K 2800/30* (2013.01); *A61K 2800/34* (2013.01)

(58) Field of Classification Search
CPC . A61Q 19/00; A61K 2800/34; A61K 2800/10
See application file for complete search history.

*Primary Examiner* — Qiuwen Mi
(74) *Attorney, Agent, or Firm* — Knobbe, Martens, Olson & Bear, LLP

(57) ABSTRACT

Embodiments of the present application relates to cosmetic compositions and cosmetic products free or substantially free of synthetic silicones. The cosmetic composition comprises one or more plant extracts rich in natural silicon (e.g., a bamboo extract), a unique blend of fatty acid esters derived from plant sources and also saccharides derived from plants.

20 Claims, No Drawings

SILICONE-FREE COSMETIC COMPOSITIONS

INCORPORATION BY REFERENCE TO PRIORITY APPLICATION

The present application claims the benefit of priority to U.S. Provisional Appl. No. 62/865,011, filed Jun. 21, 2019, which is hereby incorporated by reference in its entirety.

BACKGROUND

Field

The present application relates to cosmetic compositions and cosmetic products free or substantially free of synthetic silicones.

Description of the Related Art

Silicone fluids are widely used in toiletry, cosmetic, and personal care formulations. Most frequently used are dimethicones, cyclomethicones, and phenyl trimethicone (collectively referred to as "silicones").

When incorporated into a skin care formulation, silicones provide a variety of benefits such as improved slip or glide, reduction of tack without contributing to oiliness or greasiness and give a "dry" skin feel. However, there are certain drawbacks in using silicones in cosmetic and personal care formulations. For example, the thick coverage of the silicones are difficult to remove from the skin, and also may clog the skin pores or hair follicles. Silicones have also been implicated as potentially being harmful to the environment and biocumulative. In addition, there are possible links between silicone and silicone degradation products and the development of autoimmune system deficiencies in women with silicone breast implants.

Accordingly, there exists a need to replace silicones in cosmetic and personal care products with more natural alternatives that not only provide silicone-like benefits in formulations but also reduce or eliminate real or perceived health and environmental risks associated with silicones.

SUMMARY

Some embodiments of the present application relate to a cosmetic composition comprises:

a bamboo extract; a beetroot extract; a fatty acid ester derived from olive oil; and a fatty acid ester derived from coconut oil; wherein the composition is free or substantially free of silicones.

Some embodiments of the present application relate to a cosmetic composition comprises *Arundinaria Gigantea* ferment filtrate, saccharide isomerate, isoamyl laurate, isoamyl cocoate, and ethylhexyl olivate.

Some further embodiments of the present application relate to a cosmetic or personal care product comprising the cosmetic composition described herein. In some embodiments, the cosmetic or personal care product is free or essentially free of gluten, soy, grain, or other possible allergens. In some embodiments, the cosmetic or personal care product is free or essentially free of any ingredients derived from an animal source.

DETAILED DESCRIPTION

Embodiments of the present invention relate to silicone-free cosmetic compositions containing natural source of silicon for use as silicone replacement.

Silicon is the second most abundant element on Earth, and the third most abundant trace element in human body. It has been reported that silicon is important for optimal collagen synthesis and activation of hydroxylating enzymes, improving skin strength and elasticity. In addition, a higher silicon content in the hair fiber results in a lower rate of hair loss and increased brightness. Nails are also affected by the presence of silicon, since this is the predominant mineral in their composition.

Silicon occurs naturally in foods in the form of silicon oxide (also known as silica) and silicates, which are present in water and in plant and animal sources.

Definition

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least." When used in the context of a process, the term "comprising" means that the process includes at least the recited steps, but may include additional steps. When used in the context of a compound or composition, the term "comprising" means that the compound or composition includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

As used herein, the term "essentially free" or "substantially free" means that a composition of the present invention is free of an ingredient or only contains a trace amount of an ingredient. For example, the composition may contain less than about 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.005%, 0.004%, 0.003%, 0.002%, or 0.001% of an ingredient.

As used herein, the term "silicone" is also known as polysiloxane, refers to any synthetic polymer or compound comprising repeating units of siloxane, which is a chain of alternating silicon atoms and oxygen atoms.

Some embodiments of the present application relate to a cosmetic composition comprises:

a bamboo extract; a beetroot extract; at least one fatty acid ester derived from olive oil; and at least one fatty acid ester derived from coconut oil; wherein the composition is free or substantially free of silicones.

Various parts of the bamboo may be used to produce the bamboo extract, for example, leaf, stem, etc. In some embodiments, the bamboo extract is *Arundinaria Gigantea* extract, for example, *Arundinaria Gigantea* ferment filtrate. In one particular example, the bamboo extract is *lactobacillus Arundinaria Gigantea* ferment, which is also known as bamboo isoflavones. The amount of bamboo extract in the composition may range from about 0.01% to about 40% by weight of the total weight of the composition, or from about 0.1% to about 30% by weight or from about 1% to about 20% by weight. In some further embodiments, the amount of bamboo extract (e.g., *lactobacillus Arundinaria Gigantea* ferment filtrate) in the composition may be about 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% by weight of the total weight of the composition, or a range defined by any two of the preceding values. In some further embodiments, the amount of bamboo extract in the cosmetic product may range from about 0.01% to about 20% by weight, from about 0.1% to about 10% by weight, or from about 1% to about 5% by weight of the total weight of the product.

In some embodiments, the beetroot extract comprises saccharide isomerate. Saccharide isomerate is a deeply moisturizing ingredient based on plant sugars, for example, beet sugars. It provides deep hydration and creates a moisture reservoir that lasts for 72 hours, providing excellent moisturizing effects to the skin for extended periods of time. Saccharide isomerate (INCI) is manufactured under the tradename Pentavitin®. It has been reported that saccharide isomerate may potentially boost hyaluronic acid synthesis by 66%. In a 28-day clinical trial on 19 volunteers aged between 44 to 56 years showed that saccharide isomerate was capable of reducing the appearance of wrinkles by 18.5% to 79.3%. In some embodiments, the amount of saccharide isomerate in the composition may range from about 0.01% to about 50% by weight of the total weight of the composition, or from about 0.1% to about 40% by weight or from about 1% to about 30% by weight. In some further embodiments, the amount of beetroot extract (e.g., saccharide isomerate) in the composition may be about 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% by weight of the total weight of the composition, or a range defined by any two of the preceding values. In some further embodiments, the amount of beetroot extract (e.g., beet sugar or saccharide isomerate) in the cosmetic product may range from about 0.01% to about 25% by weight, from about 0.1% to about 10% by weight, or from about 1% to about 5% by weight of the total weight of the product.

In some embodiments, the fatty acid ester derived from olive oil comprises a reaction product of one or more fatty acids in olive oil and $C_4$-$C_{20}$ alcohol. The $C_4$-$C_{20}$ alcohol may contain one or more hydroxyl groups. In some further embodiments, the fatty acid ester derived from olive oil comprises ethylhexyl olivate, which is the reaction product of ethylhexyl alcohol with the fatty acid(s) from olive oil, for example, oleic acid, linoleic acid, and palmitic acid. In some embodiments, the weight percentage of the fatty acid ester derived from olive oil (e.g., ethylhexyl olivate) in the cosmetic composition is from about 2% to about 25%, for example, about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25%, or a range defined by any of the two preceding values. In some further embodiments, the amount of the fatty acid ester derived from olive oil (e.g., ethylhexyl olivate) in the cosmetic product may range from about 0.01% to about 10%, from about 0.05% to about 5%, or from about 0.1% to about 2.5% by weight of the total weight of the product.

Ethylhexyl olivate is an emollient. Light like oil with a dry after feel, it adds immediate moisture and is able to help retain levels of hydration over time. Its moisturizing property was measured in one corneometry test in comparison with olive Squalene. Skin hydration was significantly increased in the presence of either ethylhexyl olivate and Squalene at 30 minutes, but only the ethylhexyl olivate sustained the hydration level up to 120 minutes post-application. It was surmised that the continual moisturization of ethylhexyl olivate might be explained by its broader compatibility with the hydrolipidic film on a molecular level. Squalene would act as a single component while ethylhyexyl olivate would work as a multi-purpose ingredient. It promotes higher skin hydration and also increases the flexibility, elasticity and suppleness of the skin. It improves skin barrier integrity. It also contains nourishing phytocompounds to support healthy skin, adds a protective film with reduced greasiness, is a low viscosity emollient and is not sticky. Skin feels softer and smoother.

In some embodiments, the fatty acid ester derived from coconut oil comprises a reaction product of one or more fatty acids in coconut oil and $C_4$-$C_{20}$ alcohol. The $C_4$-$C_{20}$ alcohol may contain one or more hydroxyl groups. In some further embodiments, the fatty acid ester derived from coconut oil comprises isoamyl cocoate, which is the reaction product of isoamyl alcohol with one or more fatty acid(s) from coconut oil, for example, lauric acid, myristic acid, palmitic acid, caprylic acid, capric acid and stearic acid. Isoamyl cocoate is an ester made out of coconut and sugar beet (esterification of Isoamyl alcohol, source sugar beet, with fatty acids from coconut oil). Blended with isoamyl laurate, it demonstrated a silky slip and glide and soft after feel similar to cyclomethicone. In some embodiments, the weight percentage of the fatty acid ester derived from coconut oil (e.g., isoamyl cocoate) in the cosmetic composition is from about 2% to about 20%, for example, about 2%, 3%, 4%, 5%, 6%, 7%, 8%, 9%, 10%, 11%, 12%, 13%, 14%, 15%, 16%, 17%, 18%, 19%, or 20%, or a range defined by any of the two preceding values. In some further embodiments, the amount of the fatty acid ester derived from coconut oil (e.g., isoamyl cocoate) in the cosmetic product may range from about 0.01% to about 10%, from about 0.05% to about 5%, or from about 0.1% to about 2.5% by weight of the total weight of the product.

In some embodiments, the cosmetic composition further comprises at least one ester of $C_8$-$C_{20}$ fatty acid, for example, at least one ester of $C_8$-$C_{12}$ fatty acid, such as lauric acid, caprylic acid, or capric acid. In one embodiment, the skin care composition further comprises isoamyl laurate. Isoamyl laurate is lighter and much faster spreading than caprylic/capric triglyceride. It is able to absorb into the skin in a slower fashion, leaving a cushioned after-feel. It also offered a reduction in the "soaping effect" with the right percentages of this in our formulation. Another good quality was increased spread ability of the formula, good shelf life, and a silky feel. In some embodiments, the weight percentage of the ester of $C_8$-$C_{20}$ fatty acid (e.g., isoamyl laurate) in the cosmetic composition is from about 10% to about 30%, for example, about 10%, 11%, 12%, 13%, 14%, 15%, 16%, 17%, 18%, 19%, 20%, 21%, 22%, 23%, 24%, 25%, 26%, 27%, 28%, 29%, or 30%, or a range defined by any of the two preceding values. In some further embodiments, the amount of the ester of $C_8$-$C_{20}$ fatty acid (e.g., isoamyl laurate) in the cosmetic product may range from about 0.01% to about 20%, from about 0.1% to about 10%, or from about 1% to about 5% by weight of the total weight of the product.

In some embodiments, the cosmetic composition further comprises one or more natural silicon containing plant extracts selected from the group consisting of sugarcane extract, cogon grass extract, nettle leaf extract, horsetail extract, oat straw extract, rosehip extract, dandelion extract, raisin extract, mango extract, banana extract, carrot extract, cucumber extract, celery extract, asparagus extract, and artichoke extract.

In some embodiments, the cosmetic composition may further comprises one or more antioxidants, one or more essential oils, or combinations thereof. Non-limiting examples of antioxidants include acai oil, alpha lipoic acid, green and white tea, retinol, vitamin C, coenzyme Q10 (Co Q-10), isoflavones, polyphenols, curcumin, turmeric, pomegranate, rosemary, glutathione, selenium, and zinc.

Some embodiments of the present application relate to a cosmetic composition comprises a bamboo extract (such as *Arundinaria Gigantea* ferment filtrate), beet sugar (such as saccharide isomerate), isoamyl laurate, isoamyl cocoate, and ethylhexyl olivate. In some further embodiments, the cosmetic composition consists of, or consists essentially of *Arundinaria Gigantea* ferment filtrate, saccharide isomerate, isoamyl laurate, isoamyl cocoate, and ethylhexyl olivate, and optionally a cosmetically acceptable carrier. The combination of these esters with the fermented bamboo can provide an improved feel and spread ability, and also improve stability of the formulation, was without a strong natural odor, rapidly dried from a silky glide to a smooth, matte, velvety finish and a non-greasy application. In some embodiments, the weight percentage of the bamboo extract in the cosmetic composition is from about 10% to about 40%, for example, about 10%, 15%, 20%, 25%, 30%, 35% or 40%. In some embodiments, the weight percentage of the saccharide isomerate in the cosmetic composition is from about 10% to about 50%, for example, about 10%, 15%, 20%, 25%, 30%, 35%. 40%, 45%, or 50%. In some embodiments, the weight percentage of isoamyl laurate in the cosmetic composition is from about 10% to about 30%, for example, about 10%, 15%, 20%, 25% or 30%. In some embodiments, the weight percentage of ethylhexyl olivate in the cosmetic composition is from about 2% to about 25%, for example, about 2%, 3%, 4%, 5%, 6%, 7%, 8%, 9%, 10%, 15%, 20% or 25%. In some embodiments, the weight percentage of isoamyl cocoate in the cosmetic composition is from about 2% to about 20%, for example, about 2%, 3%, 4%, 5%, 6%, 7%, 8%, 9%, 10%, 15% or 20%.

Essential Oils

Various essential oils may be used in the present cosmetic compositions. Essential oils may act as a fragrance, or may also confer additional benefits due to the nature of the essential oils, including but not limited to cleansing, nourishing, and strengthening the hair follicles and shaft. However, most essential oils are highly concentrated and potent, and they may have adverse effect on skin if used undiluted. In certain hair and skin care products, essential oils are diluted with carrier oils. Carrier oils are a vegetable origin extracted from nuts and seeds by cold pressing. Carrier oils provide lubrication and moisture and help with the absorption of essential oils into the skin. In some embodiments of the cosmetic composition described herein, the one or more essential oils are used without any carrier oil. In some embodiments, the cosmetic composition comprises about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, or 5.0% by weight essential oils, or a range defined by any two preceding values.

Preferred embodiments of the essential oils that may be used in the present invention are described herein. In some embodiments, the one or more essential oils are selected from the group consisting of lavender oil, tea tree oil, peppermint oil, rosemary oil, and combinations thereof. Other essential oils that may be used in the present invention include, but are not limited to, allspice berry essential oil, angelica seed essential oil, anise seed essential oil, basil essential oil, bay laurel essential oil, bay essential oil, bergamot essential oil, blood orange essential oil, camphor essential oil, caraway seed essential oil, cardamom seed essential oil, carrot seed essential oil, cassia essential oil, catnip essential oil, cedarwood essential oil, celery seed essential oil, chamomile essential oil, chamomile roman essential oil, cinnamon bark essential oil, cinnamon leaf essential oil, citronella essential oil, clary sage essential oil, clove bud essential oil, coriander seed essential oil, cypress essential oil, elemi essential oil, eucalyptus essential oil, fennel essential oil, fir needle essential oil, frankincense essential oil, geranium essential oil, ginger essential oil, grapefruit essential oil, helichrysum essential oil, hop essential oil, hyssop essential oil, juniper berry essential oil, labdanum essential oil, lemon essential oil, lemongrass essential oil, lime essential oil, magnolia essential oil, mandarin essential oil, marjoram essential oil, myrrh essential oil, myrtle essential oil, neroli essential oil, niaouli essential oil, nutmeg essential oil, orange essential oil, oregano essential oil, palmarosa essential oil, patchouli essential oil, pennyroyal essential oil, pepper black essential oil, petitgrain essential oil, pine needle essential oil, radiata essential oil, ravensara essential oil, rose essential oil, rosewood essential oil, sage essential oil, sandalwood essential oil, spearmint essential oil, spikenard essential oil, spruce essential oil, star anise essential oil, tangerine essential oil, thyme red essential oil, verbena essential oil, vetiver essential oil, wintergreen essential oil, wormwood essential oil, yarrow essential oil, or Ylang Ylang Extra essential oil, or combinations thereof.

Hydrocarbons

In some instances, the composition may also contain hydrocarbons, fat, oil, or wax that are not volatile (as in contrast to the essential oils, which are very volatile). In some embodiments, the hydrocarbons may include ozokerite, α-olefin oligomer, light isoparaffin, light liquid isoparaffin, squalene, squalane, vegetable squalane, ceresin, paraffin, polyethylene powder, polybutene, microcrystalline wax, liquid isoparaffin, liquid paraffin, mineral oil and vaseline.

Fat/Wax/Non-Volatile Oil

Natural fats, wax and oils that may be suitable for the present invention include jojoba oil, carnauba wax, candelilla wax, rice wax, shellac, lanoline, mink tallow wax, spermaceti, sugar cane wax, sperm whale oil, beeswax and montan wax, argan oil, avocado oil, almond oil, olive oil, extra virgin olive oil, sesame oil, rice bran oil, rice oil, rice germ oil, corn oil, soybean oil, corn oil, persic oil, palm kernel oil, palm oil, castor oil, grape seed oil, cottonseed oil, coconut oil, hydrogenated coconut oil, beef tallow, hydrogenated oil, horse oil, mink oil, egg yolk oil, egg yolk fatty oil, rose hips oil, candlenut oil, wheat germ oil, peanut oil, camellia oil, sasanqua oil, cacao butter, Japan wax, beef bone fat, beef foot oil, hog fat, horse fat, mutton tallow, shea butter, macademia nut oil and meadowfoam seed oil.

Humectants

Humectant is a substance that attracts and retains moisture. Humectants used in cosmetic and personal care products and compositions include synthetic humectants (such as propylene glycol, urea, polyethylene glycol (PEG) and natural humectants (such as sugars, betains, amino acids, honey, aloe extract, hyaluronic acid, and glycerin. In one particular example, the humectant may include glycine betaine (*Beta vulgaris*), which is a beet sugar extract.

Unlike traditional humectants, which draw moisture from the environment, glycine betaine adds hydration directly due to it's abundant source of saccharides. The addition of this ingredient helps skin hydrates from within, making it a suitable choice for any climate or environment. Studies have shown a shampoo, containing 5% *Beta vulgaris* (beet sugar), used for six weeks, increased the hair content of Betaine by a minimum of 40%.

Surfactants and Solubilizers

In some embodiments, the cosmetic or personal care composition may further comprise one or more surfactants, or solubilizer, or combinations thereof.

Solubilizers, as used herein, refers to a compound that can help to make otherwise insoluble liquids soluble in water. For example, essential oils do not mix well with water. Mixing essential oils with a solubilizer before adding to water will help the essential oil mix well with water. Examples of solubilizers include polysorbates, safflower oleosomes, and Propanediol.

Surfactants may include fatty acids, higher monoalcohols, alkyl glyceryl ethers, esters, anionic surface active agents, cationic surface active agents, amphoteric surface active agents, and nonionic surface active agents. In some embodiments, the cosmetic compositions described herein comprise less than about 10%, 9%, 8%, 7%, 6%, 5%, 4%, 3%, 2%, 1%, 0.5% or 0.1% surfactant, or a range defined by any of the two preceding values.

In some embodiments, the cosmetic composition comprises one or more nonionic surface active agents. Non-limiting examples include polyoxyethylene(10) alkyl(12,13) ether, polyoxyethylene lauryl ether, polyoxyethylene cetyl ether, polyoxyethylene stearyl ether, polyoxyethylene oleyl ether, polyoxyethylene(3,7,12) alkyl(12-14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene(2,10,20) isostearyl ether, polyoxyethylene oleylcetyl ether, polyoxyethylene(20) arachyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene(1) polyoxypropylene(1,2,4,8) cetyl ether, polyoxyethylene(5) polyoxypropylene(1,2,4,8) cetyl ether, polyoxyethylene(10) polyoxypropylene(1,2,4,8) cetyl ether, polyoxyethylene(20) polyoxypropylene(1,2,4,8) cetyl ether, polyoxyethylene polyoxypropylene lauryl ether, polyoxyethylene(3) polyoxypropylene(34) stearyl ether, polyoxyethylene(4) polyoxypropylene(30) stearyl ether, polyoxyethylene(34) polyoxypropylene(23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, ethylene glycol monostearate (self-emulsifying), diethylene glycol laurate, polyethylene glycol myristate, polyethylene glycol palmitate, diethylene glycol stearate, polyethylene glycol(2) monostearate (self-emulsifying), polyethylene glycol isostearate, ethyleneglycol dioctanoate, diethylene glycol dilaurate, polyethylene glycol dilaurate, polyethylene glycol(150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene(20) sorbitan monolaurate, polyoxyethylene(20) sorbitan monopalmitate, polyoxyethylene (6) sorbitan monostearate, polyoxyethylene(20) sorbitan monostearate, polyoxyethylene(20) sorbitan tristearate, polyoxyethylene(6) sorbitan monooleate, polyoxyethylene (20) sorbitan monooleate, polyoxyethylene(20) sorbitan trioleate, polyoxyethylene(20) sorbitan monococoate, polyoxyethylene (10-80) sorbitan monolaurate, polyoxyethylene sorbitan tristearate, polyoxyethylene (20) sorbitan isostearate, polyoxyethylene(150) sorbitan tristearate, polyoxyethylene castor oil, polyoxyethylene hydrogenated castor oil, polyoxyethylene(10) hydrogenated castor oil, polyoxyethylene(20) hydrogenated castor oil, polyoxyethylene (40) hydrogenated castor oil, polyoxyethylene(50) hydrogenated castor oil, polyoxyethylene(60) hydrogenated castor oil, lipophilic glyceryl monostearate, lipophilic glyceryl monooleate, glyceryl monostearate (self-emulsifying), glyceryl cocoate, glyceryl laurate, glyceryl myristate, glyceryl isostearate, glyceryl ricinoleate, glyceryl monohydroxystearate, glyceryl oleate, glyceryl linoleate, glyceryl erucate, glyceryl behenate, wheat germ fatty acid glycerides, safflower oil fatty acid glycerin monoester, hydrogenated soy glyceride, saturated fatty acid glycerides, cottonseed oil glyceride, glyceryl monoisostearate monomyristate, glyceryl monotallowate, glyceryl monolanolate, glyceryl sesquioleate, glyceryl distearate, glyceryl diisostearate, glyceryl diarachate, sorbitan monolaurate, sobitan monopalmitate, sorbitan monostearate, sorbitan monoisostearate, sorbitan monooleate, sorbitan sesquistearate, sorbitan sesquioleate, sorbitan tristearate, sorbitan trioleate, sobitan monococoate, sorbitan isostearate, sorbitan sesquiisostearate, sorbitan distearate, diglyceryl isopalmitate, poly(4-10)glyceryl monolaurate, poly(10)glyceryl monomyristate, poly(2-10)glyceryl monostearate, poly(2-10)glyceryl monoisostearate, poly(2-10)glyceryl monooleate, diglyceryl sesquioleate, poly(2-10)glyceryl diisostearate, poly(6-10)glyceryl distearate, diglyceryl triisostearate, poly(10)glyceryl tristearate, poly(10)glyceryl trioleate, poly(2)glyceryl tetraisostearate, decaglyceryl pentastearate, poly(6-10)glyceryl pentaoleate, poly(10)glyceryl heptastearate, decaglyceryl decastearate, poly(10)glyceryl decaoleate, concentrated poly(6)glyceryl pentaricinoleate, sucrose fatty acid ester, sucrose cocoate, alkyl glucoside, cocodimethyl amine oxide, lauryl dimethylamine oxide, dihydroxyethyl lauryldimethylamine oxide, stearyl dimethylamine oxide, oleyl dimethyl amine oxide and polyoxyethylene cocoalkyl dimethyl amine oxide. In one embodiment, the surfactant comprises decyl glucoside, a nonionic surfactant.

In some embodiments, the surfactants that may be used in the present invention are natural surface active agents, such as saponin, lecithin, soybean phospholipid, hydrogenated soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid, mannosyl erythritol lipid, surfactin and its salts.

In some embodiments, the cosmetic composition may include at least one ultraviolet absorbing agent. Non-limiting examples include p-aminobenzoic acid, p-aminobenzoic acid derivatives, such as ethyl p-aminobenzoate, glyceryl p-aminobenzoate, amyl p-dimethylaminobenzoate and 2-ethylhexyl p-dimethylaminobenzoate, cinnamic acid derivatives, such as benzyl cinnamate, glyceryl di-p-methoxycinnamate mono-2-ethylhexanoate, methyl 2,4-diisopropylcinnamate, ethyl 2,4-diisopropylcinnamate, potassium p-methoxycinnamate, sodium p-methoxycinnamate, isopropyl p-methoxycinnamate, 2-ethylhexyl p-methoxycinnamate, 2-ethoxyethyl p-methoxycinnamate and ethyl p-ethoxycinnamate, urocanic acid, urocanic acid derivatives, such as ethyl urocanate, benzophenone derivatives, such as 2,4-dihydroxybenzophenone, 2,2',4,4'-tetrahydroxybenzophenone, 2-hydroxy-4-methoxy-5-sulfobenzophenone sodium, 2-hydroxy-4-methoxybenzophenone-5-sulfonic acid, 2-hydroxy-4-methoxybenzophenone, 2,2'-dihydroxy-4,4'-dimethoxybenzophenone and 2,2'-dihydroxy-4,4'-dimethoxy-5-sulfobenzophenone sodium, salicylic acid derivatives, such as ethylene glycol salicylate, 2-ethylhexyl salicylate, phenyl salicylate, benzyl salicylate, p-tert-butylphenyl salicylate, homomentyl salicylate and 3,3,5-trimethylcyclohexyl salicylate, 2-(2'-hydroxy-5'-methoxyphenyl)benzotriazole, and 4-tert-butyl-4'-methoxybenzoylmethane.

In some embodiments, the cosmetic composition is free or essentially free of preservatives. In some other embodiments, the cosmetic composition may comprise one or more preservatives, for example, gluconlactone, sodium benzoate, potassium sorbate, and combinations thereof. Other preservatives that may be used in the present invention include, but are not limited to, benzoic acid, undecylenic acid, salicylic acid, sorbic acid, dehydroacetic acid, sodium dehydroacetate, isobutyl parahydroxybenzoate, isopropyl parahydroxybenzoate, ethyl parahydroxybenzoate, butyl parahydroxybenzoate, propyl parahydroxybenzoate, benzyl parahydroxybenzoate, methyl parahydroxybenzoate, sodium methyl parahydroxybenzoate, and phenoxyethanol.

Other ingredients that may be used in the present compositions include pH adjustors, such as citric acid, sodium hydroxide, potassium hydroxide and triethanolamine; perfume; distilled or deionized water.

In some embodiments, the product is free or essentially free of gluten, grain or soy, or all three ingredients. In some embodiments, the product is free or essentially free of any ingredient derived from an animal source.

Some further embodiments of the present application relate to a cosmetic or personal care product comprising the cosmetic composition described herein. The cosmetic or personal care products described herein may be in various formulations, such as a cream, a lotion, a gel, a foam, a powder, an aerosol, a solution, a liquid suspension, or an emulsion (including both water-in-oil and water-in-oil emulsions), liposomes, etc. In some embodiments, the cosmetic or personal care product is a skin care product, such as a skin cream or lotion, a shampoo or hair conditioner, etc. In some embodiments, the product is free or essentially free of gluten, grain or soy. In some embodiments, the product is free or essentially free of any ingredient derived from an animal source.

EXAMPLES

Additional embodiments are disclosed in further detail in the following examples, which are not in any way intended to limit the scope of the claims.

Example 1

Cold Process Hair Conditioner with Silicone Replacement Formulation

| Phase | Ingredient | % Concentration (by weight) |
|---|---|---|
| A | Water | 79 |
|   | Glycerin | 3 |
| B | ICE (cetearyl alcohol, behentrimonium chloride, Polyquaterum 37) | 5 |
| C | Silicone Replacement formula | 7 |
|   | Hydrolyzed keratin protein | 2 |
|   | Argan Oil | 2 |
|   | Preservative: Phenoxyethenol/SA | 1.5 |
|   | Fragrance (optional) | 0.5 |
|   | TOTAL | 100.00 |

Procedure: Disinfect all containers and instruments. Weigh ingredients in Phase A and set aside. Weigh ingredients in Phase B and mix until it resembles a paste. While mixing, add Phase B to A. Add phase C, mixing after each addition. Continue to mix well for one minute or until blended. Note: Silicone replacement formulation includes the following five ingredients in the specific percentage by weight: *Arundinaria Gigantea* ferment filtrate (30.43%), saccharide isomerate (30.43%), isoamyl laurate (21.74%), isoamyl cocoate (8.69%), and ethylhexyl olivate (8.69%).

Example 2

Hand Cream with Silicone Replacement Formulation

| Phase | Ingredient | % Concentration (by weight) |
|---|---|---|
| A | Water | 63.5 |
|   | Glycerin | 3 |
| B | OliveM 1000 (cetearyl olivate, sorbitan olivate) | 5 |
|   | Cetyl alcohol | 2 |
|   | Silicone Replacement Part 1 | 4 |
|   | Jojoba oil | 6 |
|   | Shea butter | 4 |
|   | Xanthan gum | 0.2 |
|   | Babassu Oil | 6 |
| C | Panthenol | 2 |
|   | Potassium sorbate | 0.2 |
|   | Silicone Replacement Part 2 | 3 |
|   | Preservative: EuxyPE 9010 (phenoxyethanol/ethylhexlyglycerin) | 1 |
|   | Tocopherol | 0.1 |
|   | TOTAL | 100.00 |

Procedure: Disinfect all containers and instruments. Weigh Phase A and set aside. Weigh Phase B. Heat Phases A and B in separate heated containers in a water bath until 70° C. Stir to make sure B is completely melted. Mix B into A under agitation until completely homogenized. Remove from mixer. Continue to stir as formula cools to about 40° C. Add Phase C, stirring after each addition. Formula will continue to thicken as it cools. After formula has cooled completely, a test of the product on the hands showed that the mixture has the glide, silky feel, and velvet finish of silicones. Note: Silicone replacement formulation Part 1 includes the following three ingredients: isoamyl laurate, isoamyl cocoate, and ethylhexyl olivate. Silicone replacement formulation Part 2 includes the following two ingredients: fermented *Arundinaria Gigantea* extract and saccharide isomerate. Silicone replacement formulation includes the five ingredients in the specific percentage by weight: *Arundinaria Gigantea* ferment filtrate (30.43%), saccharide isomerate (30.43%), isoamyl laurate (21.74%), isoamyl cocoate (8.69%), and ethylhexyl olivate (8.69%).

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modifications and alternatives coming within the true scope and spirit of the invention.

What is claimed is:

1. A cosmetic composition comprising:
   a bamboo extract;
   a beetroot extract;
   at least one fatty acid ester derived from olive oil; and
   at least one fatty acid ester derived from coconut oil;
   wherein the bamboo extract comprises *Arundinaria Gigantea* ferment filtrate and wherein the composition is free or essentially free of silicones.

2. The cosmetic composition of claim 1, wherein the beetroot extract comprises saccharide isomerate.

3. The cosmetic composition of claim 1, wherein the fatty acid ester derived from olive oil comprises a reaction product of one or more fatty acids in olive oil and $C_4$-$C_{20}$ alcohol.

4. The cosmetic composition of claim 3, wherein the fatty acid ester derived from olive oil comprises ethylhexyl olivate.

5. The cosmetic composition of claim 1, wherein the fatty acid ester derived from coconut oil comprises a reaction product of one or more fatty acids in coconut oil and $C_4$-$C_{20}$ alcohol.

6. The cosmetic composition of claim 5, wherein the fatty acid ester derived from coconut oil comprises isoamyl cocoate.

7. The cosmetic composition of claim 1, further comprises at least one ester of $C_8$-$C_{20}$ fatty acid.

8. The cosmetic composition of claim 7, wherein the ester of $C_8$-$C_{20}$ fatty acid is isoamyl laurate.

9. The cosmetic composition of claim 1, further comprises one or more natural silicon containing plant extracts selected from the group consisting of sugarcane extract, cogon grass extract, nettle leaf extract, horsetail extract, oat straw extract, rosehip extract, dandelion extract, raisin extract, mango extract, banana extract, carrot extract, cucumber extract, celery extract, asparagus extract, and artichoke extract.

10. The cosmetic composition of claim 1, further comprises one or more antioxidants, one or more essential oils, or combinations thereof.

11. The cosmetic composition of claim 1, wherein the bamboo extract in the composition is from about 0.01% to about 40% by weight.

12. The cosmetic composition of claim 11, wherein the bamboo extract in the composition is from about 0.1% to about 20% by weight.

13. The cosmetic composition of claim 12, wherein the bamboo extract in the composition is from about 1% to about 10% by weight.

14. The cosmetic composition of claim 1, wherein the composition is free or essentially free of gluten, grain or soy.

15. The cosmetic composition of claim 1, wherein the composition is free or essentially free of any ingredient derived from an animal source.

16. The cosmetic composition of claim 1, wherein the cosmetic composition is a cream, a lotion, a solution, a liquid suspension, a gel, an oil, an emulsion, or a powder.

17. The cosmetic composition of claim 1, comprising *Arundinaria Gigantea* ferment filtrate, saccharide isomerate, isoamyl laurate, isoamyl cocoate, and ethylhexyl olivate.

18. The cosmetic composition of claim 17, wherein the bamboo extract in the composition is from about 0.1% to about 20% by weight.

19. The cosmetic composition of claim 17, further comprises one or more natural silicon containing plant extracts selected from the group consisting of sugarcane extract, cogon grass extract, nettle leaf extract, horsetail extract, oat straw extract, rosehip extract, dandelion extract, raisin extract, mango extract, banana extract, carrot extract, cucumber extract, celery extract, asparagus extract, and artichoke extract.

20. The cosmetic composition of claim 17, wherein the cosmetic composition is a cream, a lotion, a solution, a liquid suspension, a gel, an oil, an emulsion, or a powder.

* * * * *